United States Patent [19]

Lewis

[11] Patent Number: 4,686,469
[45] Date of Patent: Aug. 11, 1987

[54] METHOD AND DEVICE FOR MEASURING MAGNETIC PARTICLES IN A FLUID

[75] Inventor: Robert T. Lewis, Albany, Calif.

[73] Assignee: Tribometrics, Inc., Berkeley, Calif.

[21] Appl. No.: 764,552

[22] Filed: Aug. 12, 1985

[51] Int. Cl.$^4$ .................... G01N 27/74; G01R 33/12
[52] U.S. Cl. ................................ 324/204; 324/71.1; 340/631
[58] Field of Search .............. 324/204, 71.1, 71.4; 340/631; 73/64

[56] References Cited

U.S. PATENT DOCUMENTS

| | | | |
|---|---|---|---|
| 3,432,750 | 3/1969 | Botstiber | 324/41 |
| 3,553,672 | 1/1971 | Smith | 340/631 X |
| 4,047,814 | 9/1977 | Westcott | 356/38 |
| 4,176,545 | 12/1979 | Oddo | 324/71.4 X |
| 4,205,904 | 6/1980 | Skubich et al. | 340/631 |
| 4,219,805 | 8/1980 | Magee et al. | 340/631 |
| 4,323,843 | 4/1982 | Batham | 324/204 |
| 4,492,921 | 1/1985 | Sandulyak et al. | 324/204 |
| 4,500,839 | 2/1985 | Jones et al. | 324/204 |

FOREIGN PATENT DOCUMENTS

| | | | |
|---|---|---|---|
| 2931412 | 2/1981 | Fed. Rep. of Germany | 324/204 |
| 0054956 | 3/1984 | Japan | 324/204 |
| 2029580 | 3/1980 | United Kingdom . | |

Primary Examiner—Gerard R. Strecker

[57] ABSTRACT

A method and device for measuring the amount of magnetic particles in a fluid such as ferrous wear particles in the lubricant of a machine. The particles are entraped by contacting a volume of the fluid with a means to entrap the particles and magnetized by subjecting the entraped particles to a magnetic field. The amount of magnetic particles entraped is measured by measuring the magnetization of the entraped and magnetized particles.

4 Claims, 4 Drawing Figures

METHOD AND DEVICE FOR MEASURING MAGNETIC PARTICLES IN A FLUID

FIELD OF THE INVENTION

This invention is in the field of measuring magnetic particles in a fluid such as ferrous wear particles in the lubricant of a machine.

BACKGROUND OF THE INVENTION

It is well known that lubricants are commonly used to minimize wear in operating machines such as transmissions, gearboxes and engines used in aircraft, ships, locomotives, trucks and stationary machines to name a few. However, in spite of lubrication, particles wear from rubbing or bearing surfaces and deposit in the lubricant. It has long been recognized that knowledge about these wear particles in the lubricant can give valuable insight concerning the condition of the surfaces. In an aircraft engine, for example, such knowledge has been used to give early warning of engine failure. In many cases such knowledge has also been found useful in scheduling maintenance and repair. One current method to obtain this knowledge is to periodically sample the lubricant and submit it for laboratory analysis. A Spectrometric Oil Analysis Program called SOAP is used by many machine operators both military and civilian throughout the world. However, this method suffers from the delay between lubricant samplying, analysis, and the report of results to the machine operator. In addition, usually only the lubricant is analyzed and not the filter commonly present in lubricant systems. However, it is the filter, designed to entrap foreign particles, that contains most of the wear particles. This is particularly true of the larger particles produced when an abnormal wear condition is present. Since many of the rubbing or bearing surfaces in machines are made of cast iron or steel, the wear particles from these surfaces are ferrous which are magnetic.

Description of Prior Art

A great number of devices have been described for measuring magnetic particles in a fluid, such as ferrous wear particles in the lubricant of a machine. Such devices have included magnetic chip detectors to indicate the presence of large magnetic chips in oils and the like. Previous patents in this general area include the following: Botstiber in U.S. Pat. Nos. 3,432,750; Westcott in 4,047,814; Magee et al in 4,219,805; Batham in 4,323,843; Sandulyak et al in 4,492,921 and Jones et al in 4,500,839. However, these devices suffer from one or more limitations. None use a filter to entrap the particles or a measurement of magnetization to determine the amount of magnetic particles entrapped. Magnetization is the most direct indicator of the amount of magnetic particles because it discriminates against nonmagnetic particles. Nonmagnetic particles can give a false reading if some other quantity such as conductivity or optical density is measured.

SUMMARY OF THE INVENTION

It is an object of this invention to provide an improved method and device for measuring magnetic particles in a fluid, such as ferrous wear particles in the lubricant of a machine.

It is a further object of this invention to provide an improved method and device which can be used for measuring ferrous wear particles in the lubricant of a machine on line during operation.

It is a still further object of this invention to incorporate this method in a device which can use a filter to entrap the particles. Said filter could be the principle filter or it could be a supplemental filter in the lubricant system of a machine.

These and other objects are achieved by contacting the fluid containing magnetic particles with a means to entrap the magnetic particles. Said means to entrap could be virtually any filter material such as paper, cloth, ceramic, plastic or metal, to name a few, with holes sized to pass the fluid but not the particles. One can entrap and measure only magnetic particles larger than some desired size by choosing a filter material with holes of the desired size. Or said means to entrap could be magnetized ferromagnetic matrix such as steel screen, grid, mesh or wool to preferentially entrap magnetic particles. One can entrap and measure only particles with magnetizations larger than some desired magnetization by choosing the appropriate ferromagnetic matrix. The entrapped particles are subjected to a magnetic field of sufficient strength to at least partially magnetize the particles. As magnetic particles collect on said means to entrap, its magnetization increases in proportion. Measurement of the increase in the magnetization of said means to entrap is used to measure the amount of magnetic particles in the fluid after a volume of fluid has contacted said means to entrap. If said means to entrap is a filter material with holes sized to pass the fluid but not the particles, it is not necessary to subject the particles to a magnetic field during entrapment but only during the measurement of magnetization. If said means to entrap is a magnetized ferromagnetic matrix, the magnetic field serves to magnetize both said matrix and the particles.

The method and device of this invention are useful for virtually any fluid, including both liquid and gaseous fluids, containing magnetic particles. The particles could be either electrically conducting or nonconducting.

DETAILED DESCRIPTION OF THE INVENTION

Figure 1:
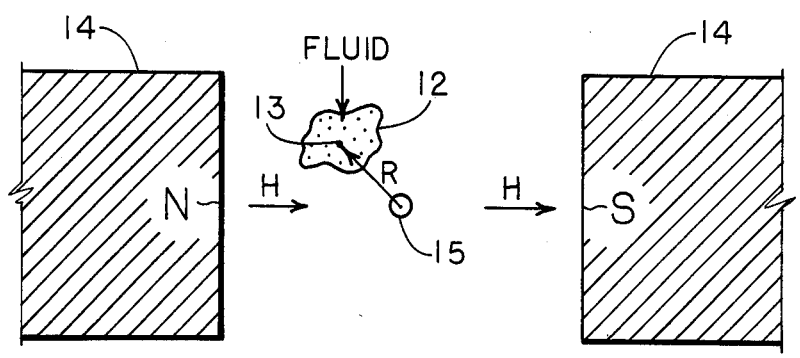
FIG. 1 illustrates one means for carrying out the method of this invention.

One means for carrying out the method of this invention is illustratedin FIG.1. The fluid contianing magnetic particles is contacted with a means to entrap, generally designated 12, entrapped the magnetic particles shown by 13 as an example. The entrapped particles are magnetized by the magnetic field H of a magnet, generally designated 14, with north and south poles marked N and S, respectively. The entrapped and magnetized particle 13 contributes an additional magnetic field proportional to its magnetization at a field measuring means, generally designated 15, positioned a vector distance R from the entrapped particle 13. The total magnetization of all entrapped and magnetized particles is determined from the resultant field of all the particles, taking into account their individual vector distances R to means 15. Any other suitable means for measuring magnetization could be used including force magnetometers, vibrating sample magnetometers, vibrating coil magnetometers, induction voltage methods or superconducting quantum interference devices to name a few. Some specific examples of spatial distributions of entrapped particles relative to means 15 for measuring the resultant field are shown below as illustration.

Figure 2:
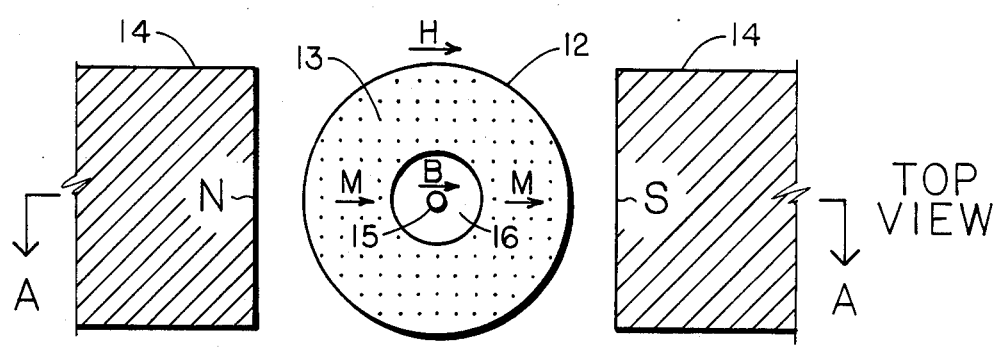
FIG. 2 is an example of a distribution of entrapped particles.
Figure 2:
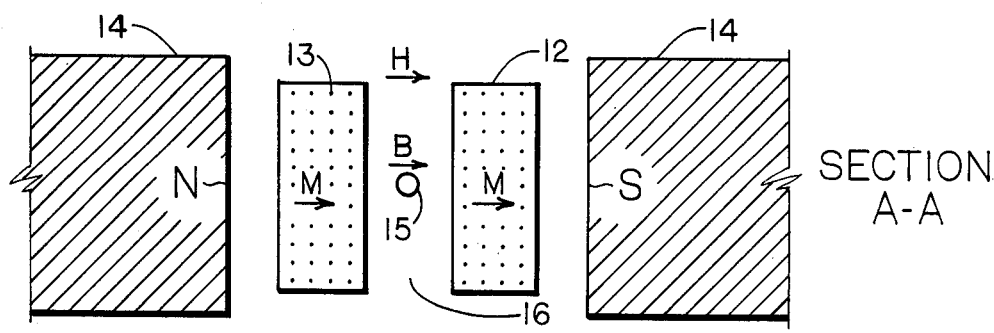

The first example is shown in FIG.2. In this example the particles are homogeneously distributed in a means to entrap 12 contributing a magnetization M to means 12. If means 12 contains a long circular hole 16 substantially perpendicular to the magnetic field H of a magnet 14 then a field B measured by a field measuring means 15 located in hole 16 contains a contribution from M and is given by $B = H + M/2$.

Figure 3:
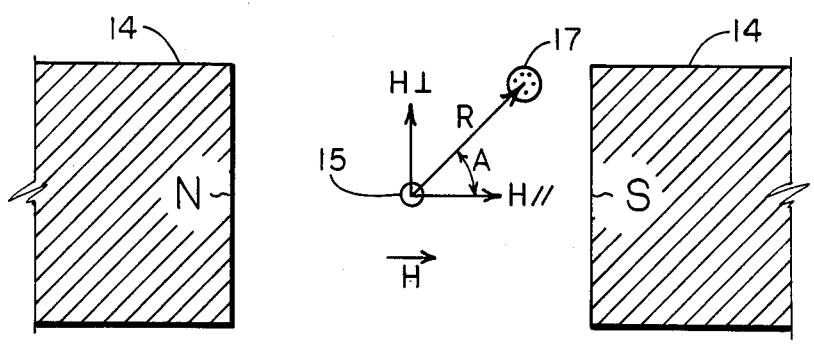
FIG. 3 is another example of a distribution of entrapped particles.

In another example, shown in FIG.3, the particles are entrapped in a volume 17 located a vector distance R from the field measuring means 15. The field at means 15 contains a contribution proportional to the magnetization of the particles in volume 17. The contribution has a component, $H//$, parallel to the field H of magnet 14 and a component, $H\perp$, perpendicular to the field H of magnet 14. If means 15 is oriented to measure the parallel component $H//$, then the field measured is maximum when an angle A between the vector distance R and the magnetic field H is equal to zero. If means 15 is oriented to measure the perpendicular component $H\perp$, then the field measured is maximum when angle A is equal to 45 degrees. In any case, the contribution of the field from the entrapped particles is greatest when the particles are located close to means 15.

It should be understood that the above examples of spatial distributions of entrapped particles relative to said means for measuring their resultant field are presented for illustration and do not limit this invention to any particular distribution.

SPECIFIC EMBODIMENTS

The method and device of this invention are particularly useful for measuring ferrous wear particles in the lubricant of a machine containing cast iron or steel rubbing or bearing surfaces. During operation of the machine, particles wear from these surfaces and deposit in the lubricant. Knowledge about the amount of these particles in the lubricant can give valuable insight concerning the condition of these surfaces. For example, a large or sudden increase in the amount indicates that an abnormal wear condition has appeared.

Some machines have a circulating lubricant flow system. In such systems lubricant is pumped from a reservoir through a filter, directed over the rubbing or bearing surfaces, and returned to the reservoir. The device illustrated in FIG. 4 could be installed in a circulating lubricant flow system of a machine. It could be installed in the return line after the lubricant has passed over the rubbing or bearing surfaces but before returning to the reservoir or it could be installed after being pumped from the reservoir but before entering the filter of the lubricant flow system. Alternatively, since the device in this embodiment uses a filter, it could replace the filter normally present in the system. In any case it could be in series with the system so as to accept the entire lubricant flow or in parallel so as to accept a representative fraction of the flow.

Figure 4:
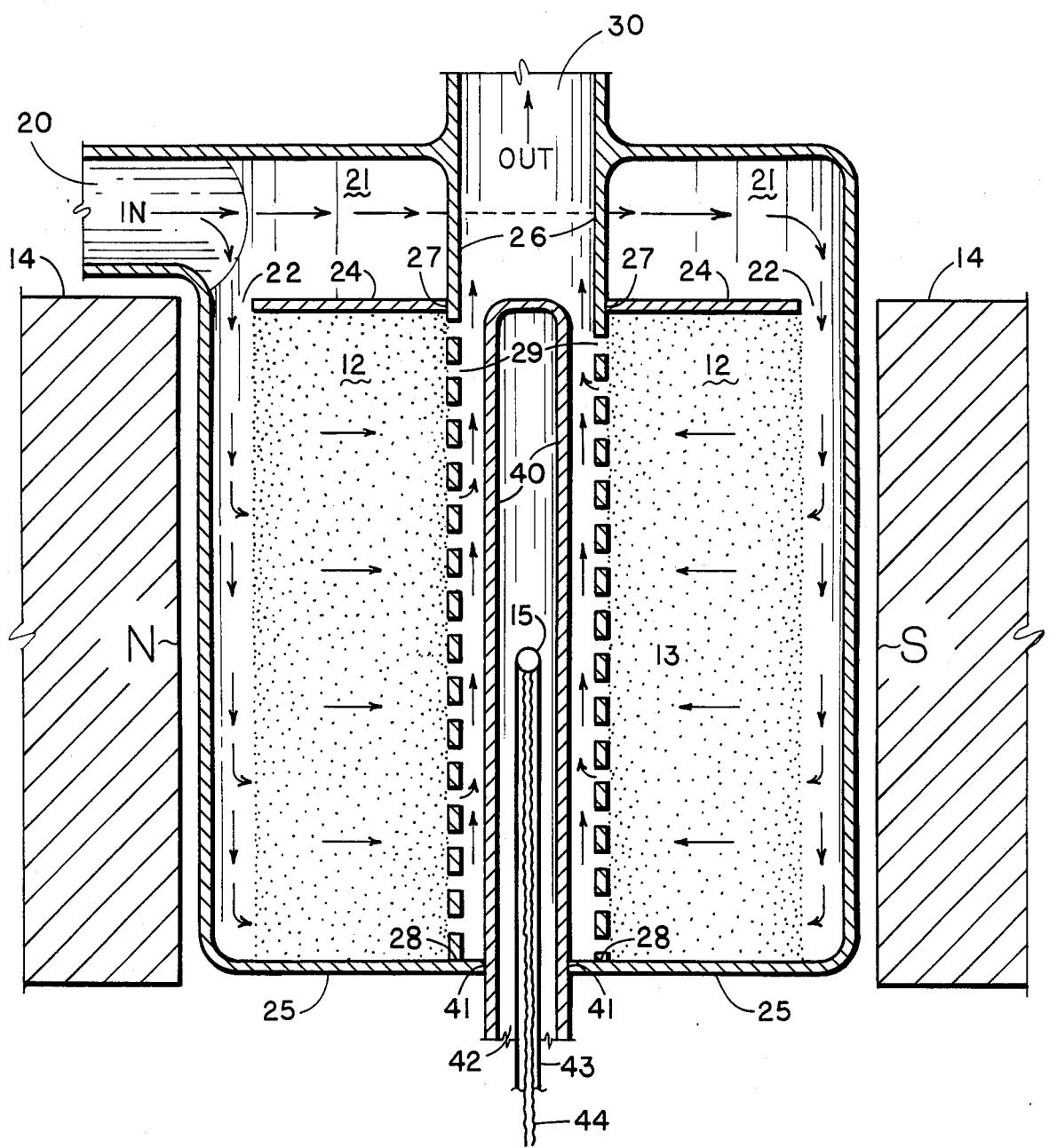
FIG. 4 shows a sectional view of an embodiment which could be installed in the circulating lubricant flow system of a machine.

The flowing lubricant is introduced into the device illustrated in FIG. 4 through inlet tube 20 from which it flows into chamber 21 and hence into cylindrical annular space 22. Annular space 22 surrounds a filter 12 typically made of paper. Other suitable filter materials include cloth, ceramic, plastic or metal to name a few. Filter 12 is selected to pass lubricant but to entrap particles larger than some desired size, appropriate for each machine, usually between about 0.5 and 200 μm. The top and bottom of filter 12 are sealed with top and bottom plates 24 and 25, respectively, to prevent the lubricant from bypassing filter 12. Top plate 24 and bottom plate 25 are also sealed to the circumference of tube 26 at positions 27 and 28, respectively. Filter 12 surrounds tube 26. Tube 26 has a perforated wall with holes 29 between positions 27 and 28 so that lubricant that passes through filter 12 will enter tube 26 and flow to outlet tube 30.

A magnet 14 is positioned so that the particles entrapped in filter 12, shown by 13 as an example, are in the magnetic field created by magnet 14. Magnet 14 has a north pole and a south pole shown respectively by N and S so that the field H of magnet 14 between the north and south poles is substantially perpendicular to the axis of tube 26. Magnet 14 could be either a permanent magnet or an electromagnet with a field H preferably at least 0.01T and more preferably at least 0.1T to magnetize the ferrous particles entrapped in filter 12.

A probe sheath 40, impervious to lubricant, is positioned inside tube 26 and sealed to bottom plate 25 at position 41. Probe sheath 40 is closed at the top but open at the bottom with an opening 42 so that a probe 43 may be inserted into probe sheath 40. Probe 43 has a magnetic field measuring means 15, typically a Hall type sensor, on its end and includes electrical connections 44 so that the field sensed by means 15 can be transmitted to appropriate equipment to read the field sensed. Any other suitable field measuring means could be used including a moving coil or a nuclear magnetic resonance oscillator to name a few. Means 15 is preferably positioned in tube 26 in the center of filter 12. However, means 15 can be moved to scan the strength of the field when desired, for example, to determine the difference between the fields inside and outside filter 12. Means 15 can include standard methods for thermal insulation, temperature control and compensation.

The device illustrated in FIG. 4 is used by flowing lubricant through the device for a time, appropriate for each machine, to entrap ferrous wear particles from the lubricant. it could be done continously; or it could be done for a specified time interval periodically, for example, for an hour once a day. When a magnetic field H is present between the north and south pole faces of magnet 14, the entrapped ferrous wear particles become magnetized with a magnetization M. A magnetic field B within sheath 40 contains a contribution from the magnetization M of the entrapped particles. If tube 26 is a long cylindrical tube whose axis is substantially perpendicular to H, then $B = H + M/2$. Since a magnetic field is not required to entrap particles in this embodiment, magnet 14 and probe 43 with means 15 need only be in position during field measurement.

Before lubricant has passed through the device, the field measured by means 15 is H. After lubricant has passed through the device for the appropriate time, ferrous wear particles larger than the desired size will have been entrapped and magnetized with a corresponding magnetization M and field B. The difference between fields B and H is a measure of the amount of the entrapped ferrous wear particles. The difference between fields B and H is measured at times appropriate for each machine. A large or sudden increase indicates a corresponding increase in the amount of ferrous wear particles in the lubricant and the appearance of an abnormal wear condition.

In some cases knowledge of the amount of particles in more than one size range is desired. This knowledge can easily be provided using the device of this embodiment. It could be done, for example, by having a series of devices each using a filter selected to entrap particles of a progressively smaller size in the direction of fluid flow.

Except where otherwise specified, the above specific embodiments of this invention are preferably made of nonmagnetic materials such as aluminum, brass, copper, austenitic stainless steel, or plastic to name a few.

I claim:

1. A device for measuring the amount of magnetic particles in a flowing fluid comprising:
   a filter with holes sized to pass the fluid but entrap the particles;
   a magnet with a magnetic field of sufficient strength to magnetize said particles positioned to have said filter in said magnetic field;
   a long cylindrical tube located within said filter and having an opening to the outside of said filter, with the axis of said tube perpendicular to the magnetic field of said magnet; and a magnetic field measuring means positioned within said cylindrical tube through said opening.

2. The device of claim 1 wherein the major dimension of said holes is between about 0.5 and 200 micrometers.

3. The device of claim 1 wherein the strength of said magnetic field is at least 0.1T.

4. A method for measuring the amount of magnetic particles in a flowing fluid comprising:
   flowing said fluid through a filter with holes sized to pass the fluid but entrap the particles;
   subjecting said filter to the field of a magnet of sufficient strengh to magnetize said particles; and
   measuring the magnetic field from said magnetized particles with a magnetic field measuring means inserted from the outside of said filter through an opening in a long cylindrical tube located within said filter with the long axis of said tube perpendicular to the magnetic field of said magnet.

* * * * *